United States Patent
Guo et al.

(10) Patent No.: US 10,806,589 B2
(45) Date of Patent: Oct. 20, 2020

(54) HIPBONE PROSTHESIS

(71) Applicant: Beijing AK Medical Co., Ltd., Beijing (CN)

(72) Inventors: Wei Guo, Beijing (CN); Caimei Wang, Beijing (CN); Tao Ji, Beijing (CN)

(73) Assignee: BEIJING AK MEDICAL CO., LTD., Beijing (CN)

( * ) Notice: Subject to any disclaimer, the term of this patent is extended or adjusted under 35 U.S.C. 154(b) by 32 days.

(21) Appl. No.: 16/316,104

(22) PCT Filed: Jul. 8, 2016

(86) PCT No.: PCT/CN2016/089488
§ 371 (c)(1),
(2) Date: Jan. 8, 2019

(87) PCT Pub. No.: WO2018/006430
PCT Pub. Date: Jan. 11, 2018

(65) Prior Publication Data
US 2019/0125539 A1 May 2, 2019

(51) Int. Cl.
*A61F 2/30* (2006.01)
*A61F 2/34* (2006.01)
(Continued)

(52) U.S. Cl.
CPC ............... *A61F 2/34* (2013.01); *A61F 2/28* (2013.01); *A61F 2/32* (2013.01); *A61F 2/3609* (2013.01);
(Continued)

(58) Field of Classification Search
CPC .. A61F 2002/30995; A61F 2002/30738; A61F 2/30988; A61F 2/28; A61F 2/30; A61B 17/7011
See application file for complete search history.

(56) References Cited

U.S. PATENT DOCUMENTS 6,413,259 B1   7/2002  Lyons
6,416,553 B1 * 7/2002  White ................... A61F 2/4637
                                                           623/22.38
(Continued)

FOREIGN PATENT DOCUMENTS

CN      1703211 A    11/2005
CN    101390781 A     3/2009
(Continued)

OTHER PUBLICATIONS

International Search Report for corresponding application PCT/CN2016/089488 filed Jul. 8, 2016; dated Mar. 31, 2017.
European Search Report for corresponding application EP16907934; Report dated Feb. 7, 2020.

*Primary Examiner* — Jason-Dennis N Stewart
(74) *Attorney, Agent, or Firm* — Cantor Colburn LLP (57) ABSTRACT

The present disclosure provides a hipbone prosthesis, comprising: a prosthesis main body (10), the prosthesis main body (10) being of an arched structure, the prosthesis main body including a first end portion (11) and a second end portion, and the first end portion (11) being contacted and matched with a sacrum (1); and an acetabular cup (20) and a connecting device (30), the acetabular cup (20) being connected with the second end portion in a position adjustable manner via the connecting device (30). According to the technical solutions of the present disclosure, the problems of unreliable supporting and easy fatigue break of a screw-rod system in the related technology are effectively solved.

9 Claims, 5 Drawing Sheets

(51) Int. Cl.
*A61F 2/32* (2006.01)
*A61F 2/28* (2006.01)
*A61F 2/36* (2006.01)
*A61F 2/46* (2006.01)

(52) U.S. Cl.
CPC ......... *A61F 2/30749* (2013.01); *A61F 2/4601* (2013.01); *A61F 2/4607* (2013.01); *A61F 2002/3611* (2013.01); *A61F 2220/0025* (2013.01)

(56) References Cited

U.S. PATENT DOCUMENTS

| | | | |
|---|---|---|---|
| 7,635,391 B2 | 12/2009 | Karrer | |
| 2006/0161261 A1* | 7/2006 | Brown | A61F 2/34 623/22.22 |
| 2007/0191839 A1 | 8/2007 | Justis | |
| 2016/0106477 A1 | 4/2016 | Hynes | |

FOREIGN PATENT DOCUMENTS

| | | | |
|---|---|---|---|
| CN | 102293681 A | 12/2011 | |
| CN | 102697585 A | 10/2012 | |
| CN | 106037994 A | 10/2016 | |

* cited by examiner

HIPBONE PROSTHESIS

TECHNICAL FIELD

The present disclosure relates to the field of medical devices, and more particularly, to a hipbone prosthesis.

BACKGROUND

Pelvis is a site more prone to bone tumors. Pelvic tumors can be classified into primary tumors and metastatic tumors. The former mainly are chondrosarcoma, osteosarcoma and ewing sarcoma, while the later are often seen in bone metastasis of mastocarcinoma, renal carcinoma, prostate carcinoma and lung carcinoma, etc. The pathogenesis of the pelvic tumors is concealed, the early diagnosis is difficult, and when it is found, the invasion extent has been expanded greatly. In addition, the dissection around the pelvis is complex because many important organs are adjacent to it. In this sense, an operation is difficult and has various complications, poor efficacy and high mortality rate. Currently, a hemipelvectomy or an improved hemipelvic-excision limb amputation is mainly adopted for the pelvic tumors. However, the excision of any pelvic tumor will cause a bone defect, and will interrupt the continuity of a trunk and lower limbs of a patient, so that the patient stands difficultly and walks with a load, and cannot bear any weight. Moreover, the patient feels painful in walking and the acetabulum inclines inward and moves up after long-time loaded walking. Once the pelvis inclines, a vertebral column bends laterally, and thus, the life quality of the patient is seriously decreased after the operation.

Before 1970s, most malignant bone tumors in a pelvic region need to receive the hemipelvectomy. Traditionally, the hemipelvectomy refers to simultaneously excise the pelvis with a pathological change and a lower limb at a same side, resulting in severe disability of the patient. Along with the development of auxiliary therapies such as chemotherapy and radiotherapy, the advent of advanced imaging approaches and the improvement of various operative techniques, some tumors which can be treated only by an amputation formerly also may be received with a limb salvage operation, so the disability of the patient is greatly reduced. Up to now, more than 80% of patients with the pelvic malignant tumors have received the limb salvage treatment.

Because of a complex anatomical structure of the pelvic region, the limb salvage operation for pelvic malignant bone tumors is quite challenging. A pelvic ring is composed of a sacrum, and hipbones at two sides. The hipbone at each side is composed of an ilium, an ischium and a pubis. With the wide excision of the pelvic tumors, the relatively large bone defect is generally caused, the continuity of the pelvis is interrupted and partial soft tissues at the periphery are lost. A Musculoskeletal Tumor Society comes up with type classification for pelvic tumor excision, and according to an anatomic site (ilium: I region; acetabulum area: II region; obturator area: III region), operation types are classified into I type (ilium excision), II type (acetabulum excision), III type (obturator excision) and IV type (sacrum involved excision). If two or more regions are excised simultaneously, an excision type is a combination of corresponding regions, for example, the ilium and the acetabulum are excised simultaneously, the operation type is the I and II type, if the whole pelvis is excised, it is the I, II and III type; and if a femoral head is excised simultaneously, it is the H type (such as II H, I and II H, II and III H).

After the pelvic tumor excision, it is very critical to reconstruct the pelvic ring. In this way, the weight of the trunk may be conducted to the lower limbs. For reconstruction of the defective pelvis, methods are different depending on experience of an operator and a condition of the patient. And the common reconstruction methods are exclusion, hip joint displacement, bone fusion, structural allogenic bone transplantation, artificial prosthesis and artificial prosthesis combined allogeneic bone transplantation.

The traditional method cannot reconstruct the defects (ilium, acetabulum and puboischium) of the whole hemipelvis. And therefore, the present disclosure aims to solve a defect reconstruction problem after the hemipelvectomy.

SUMMARY

Some embodiments of the present disclosure provide a hipbone prosthesis, so as to solve the problems of unreliable supporting and easy fatigue break of a screw-rod system in the related technology.

To this end, an embodiment of the present disclosure provides a hipbone prosthesis, including: a prosthesis main body, the prosthesis main body being of an arched structure, the prosthesis main body including a first end portion and a second end portion, and the first end portion being contacted and matched with a sacrum; and an acetabular cup and a connecting device, the acetabular cup being connected with the second end portion in a position adjustable manner via the connecting device.

In an exemplary embodiment, the connecting device includes a first connection portion and a second connection portion; a central line of the first connection portion and a central line of the second connection portion form an angle; the second end portion is provided with a third connection portion connected with the first connection portion; and the acetabular cup is provided with a fourth connection portion connected with the second connection portion.

In an exemplary embodiment, the first connection portion is a first axial tooth portion; the second connection portion is a second axial tooth portion; the third connection portion is a third axial tooth portion; the fourth connection portion is a fourth axial tooth portion; the first axial tooth portion is matched with the third axial tooth portion, so as to enable an angle between the prosthesis main body and the connecting device to be adjustable; and the second axial tooth portion is matched with the fourth axial tooth portion, so as to enable an angle between the acetabular cup and the connecting device to be adjustable.

In an exemplary embodiment, the first axial tooth portion and the third axial tooth portion are connected together via a first fastener; and the second axial tooth portion and the fourth axial tooth portion are connected together via a second fastener.

In an exemplary embodiment, an annular groove is provided on an inner wall of the acetabular cup.

In an exemplary embodiment, a plurality of through holes are provided on a cup wall of the acetabular cup.

In an exemplary embodiment, the hipbone prosthesis further includes a screw-rod structure; the screw-rod structure include connecting seat and a rod body; the connecting seat is connected with the prosthesis main body; the rod body is fixed on the connecting seat; a screw hole is formed in the first end portion; a screw seat is arranged in the screw hole; and the screw seat is provided with a spherical inner surface.

In an exemplary embodiment, the connecting seat includes: a connecting screw, one end of the connecting screw being connected with the prosthesis main body, and the other end of the connecting screw being provided with a spherical screw head; and a rod body fixing portion configured to fix the rod body, one end of the rod body fixing portion being provided with a spherical inner wall matched with the spherical screw head so that the rod body fixing portion is rotatably arranged on the connecting screw.

In an exemplary embodiment, the rod body fixing portion includes a U-shaped support and a fixing cap; and the rod body is arranged between the U-shaped support and the fixing cap in a clamping manner.

In an exemplary embodiment, anti-dropping mechanism is arranged on the prosthesis main body; the anti-dropping mechanism is arranged between the prosthesis main body and the connecting seat in a clamping manner; and the anti-dropping mechanism includes a first anti-dropping tentacle matched with a screw accommodated in the screw hole.

In an exemplary embodiment, the anti-dropping mechanism further includes an anti-dropping main body; the anti-dropping main body is arranged between the prosthesis main body and the connecting seat in a clamping manner; the anti-dropping mechanism further includes a second anti-dropping tentacle; the first anti-dropping tentacle and the second anti-dropping tentacle are connected with the anti-dropping main body and are extended outward; and a limiting sleeve matched with the rod body is arranged on the second anti-dropping tentacle.

By applying the technical solutions of the present disclosure, the hipbone prosthesis includes the prosthesis main body, the acetabular cup and the connecting device. The first end portion of the prosthesis main body is contacted and matched with the sacrum, and the acetabular cup is contacted and matched with the acetabulum. As the above-mentioned prosthesis main body is of the arched structure, the good mechanical property is obtained, and the internal force distribution of the structure is improved. Under the condition of bearing a relatively high stress and a relatively high shear force, the rigidity of the hipbone prosthesis can be maintained, so that a bone is not damaged easily. Therefore, the above-mentioned structure solves the problem that the bone is easily damaged due to the unreliable supporting and the easy fatigue break of the screw-rod system in the related technology. And in addition, by applying the technical solutions of the present disclosure, the acetabular cup is connected with the second end portion of the prosthesis main body in the position adjustable manner via the connecting device, so that a doctor can adjust a position of the acetabular cup according to a practical condition of the patient, and the acetabular cup is guaranteed to be in a good installation angle.

BRIEF DESCRIPTION OF THE DRAWINGS

The accompanying drawings are described here to provide further understanding of the present disclosure, and form a part of the present disclosure. The schematic embodiments and description of the present disclosure are adopted to explain the present disclosure, and do not form improper limits to the present disclosure. In the drawings.

In the drawings, the above accompanying drawings include the following labels:

1. a sacrum; 10. a prosthesis main body; 11. a first end portion; 111. a screw screw hole; 20. an acetabular cup; 21. an annular groove; 22. a through hole; 23. a connecting device; 41. a first axial tooth portion; 42. a third axial tooth portion; 51. a second axial tooth portion; 52. a fourth axial tooth portion; 61. a connecting seat; 611. a connection screw; 6111. a spherical screw head; 612. a rod body fixing portion; 6121. a U-shaped support; 6122. a fixing cap; 62. a connecting seat; 621. a connection screw; 6211. a spherical screw head; 622. a rod body fixing portion; 6221. a U-shaped support; 6222. a fixing cap; 63. a rod body; 70. an anti-dropping mechanism; 71. a first anti-dropping tentacle; 72. an anti-dropping main body; 73. a second anti-dropping tentacle; 74. a limiting sleeve.

DETAILED DESCRIPTION OF THE EMBODIMENTS

It is to be noted that the embodiments of the present application and the characteristics of the embodiments may be combined with each other if there is no conflict. The present disclosure is described below with reference to the drawings and embodiments in detail.

Figure 1:
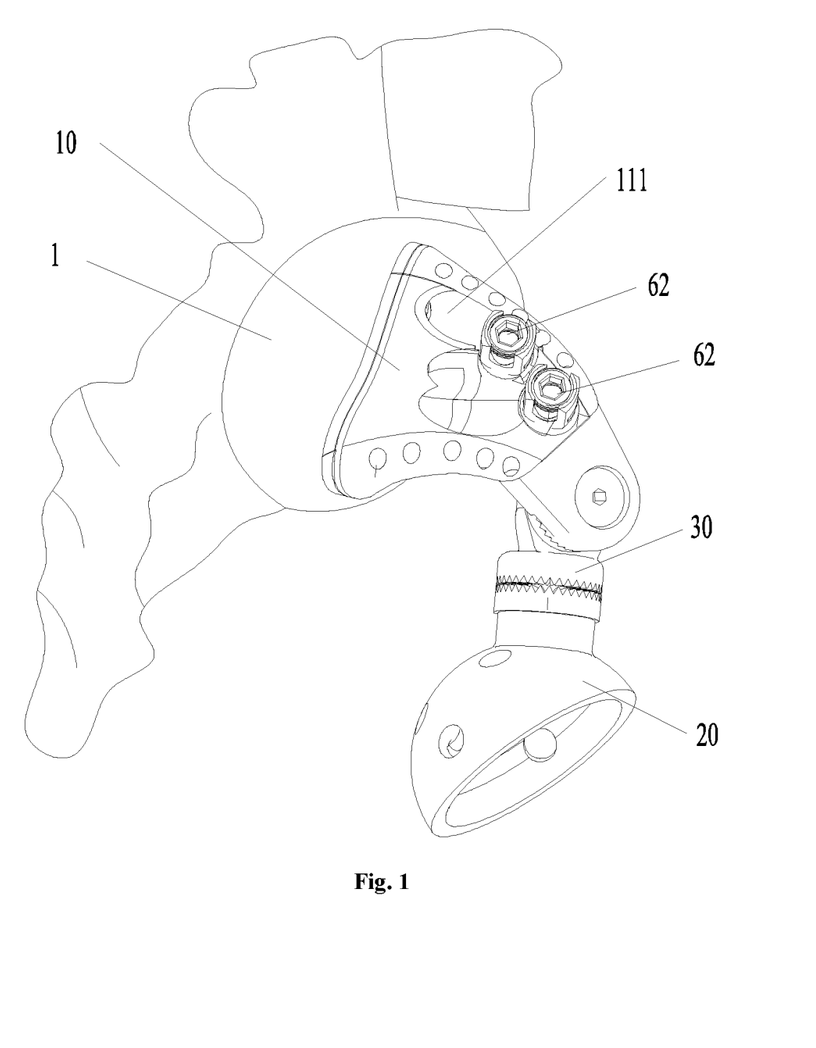
FIG. 1 shows a three-dimensional structure schematic diagram of a sacrum matched with a hipbone prosthesis of an embodiment of the present disclosure.
Figure 2:
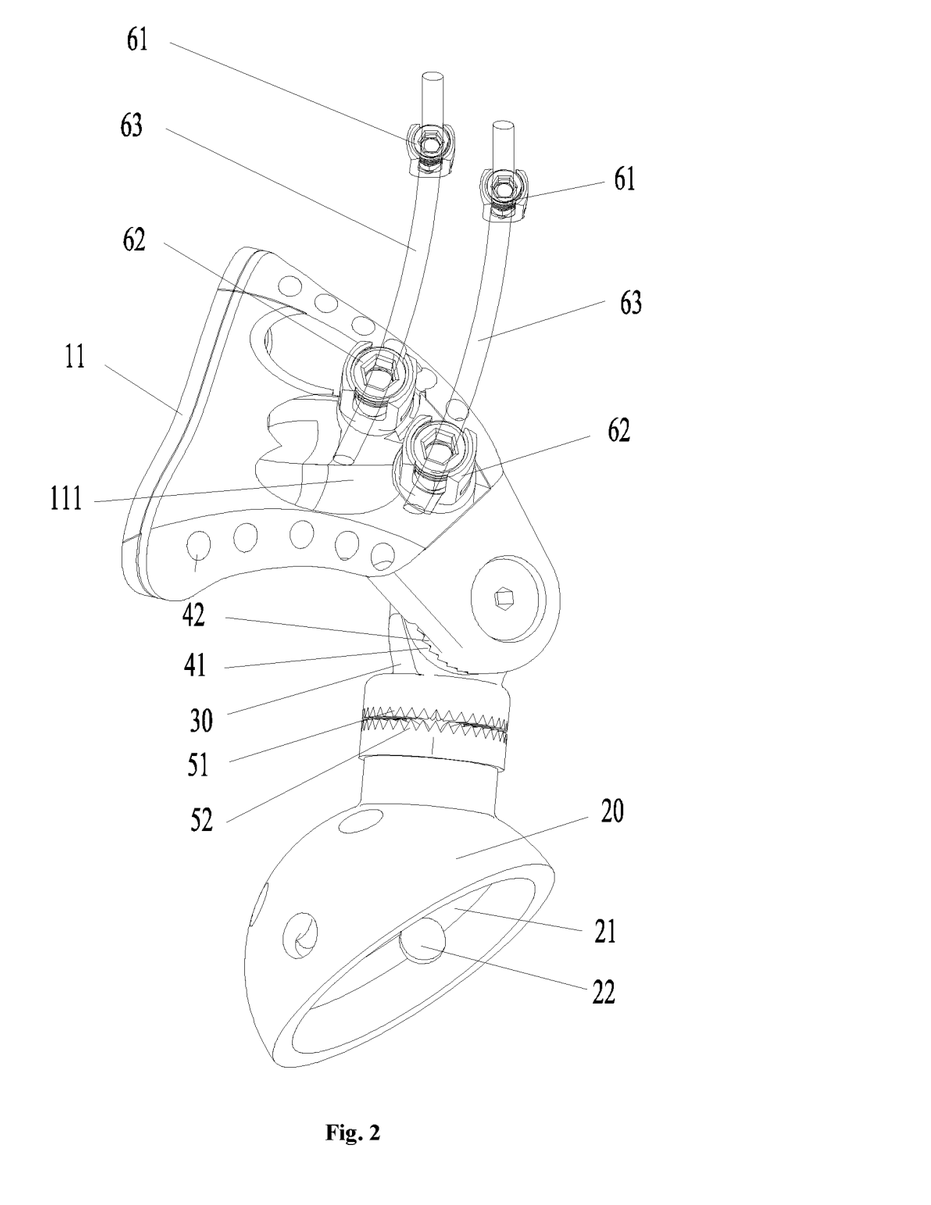
FIG. 2 shows a three-dimensional structure schematic diagram of the hipbone prosthesis in FIG. 1.

As shown in FIG. 1 and FIG. 2, a hipbone prosthesis in the embodiment includes a prosthesis main body 10, an acetabular cup 20 and a connecting device 30, wherein the prosthesis main body 10 is of an arched structure, the prosthesis main body 10 includes a first end portion 11 and a second end portion; the first end portion 11 is contacted and matched with a sacrum 1; and the acetabular cup 20 is connected with the second end portion in a position adjustable manner via the connecting device 30.

By applying the technical solutions of the present disclosure, the hipbone prosthesis includes the prosthesis main body 10, the acetabular cup 20 and the connecting device 30. The first end portion 11 of the prosthesis main body 10 is contacted and matched with the sacrum 1, and the acetabular cup 20 is contacted and matched with the acetabulum. As the above-mentioned prosthesis main body 10 is of the arched structure, the good mechanical property is obtained, and the internal force distribution of the structure is improved. Under the condition of bearing a relatively high stress and a relatively high shear force, the rigidity of the hipbone prosthesis can be maintained, so that a bone is not damaged easily. Therefore, the above-mentioned structure solves the problem that the bone is easily damaged due to the unreliable supporting and the easy fatigue break of the screw-rod system in the related technology. And in addition, by applying the technical solutions of the present disclosure, the acetabular cup 20 is connected with the second end portion of the prosthesis main body 10 in the position adjustable manner via the connecting device 30, so that a doctor can adjust a position of the acetabular cup according to a practical condition of the patient, and the acetabular cup 20 is guaranteed to be in a good installation angle; and thus, the postoperative recovery of the patient is better.

As shown in FIG. 1 and FIG. 2, in the embodiment, the connecting device 30 includes a first connection portion and a second connection portion; a central line of the first connection portion and a central line of the second connection portion form an angle; the second end portion is provided with a third connection portion connected with the first connection portion; and the acetabular cup 20 is provided with a fourth connection portion connected with the second connection portion. Specifically, when the doctor adjusts the position of the acetabular cup 20, the acetabular cup 20 not only may rotate around the central line of the first connection portion, but also may rotate around the central line of the second connection portion. In this way, the doctor can adjust the position of the acetabular cup more accurately to be more suitable for the practical condition of the patient; and thus, the postoperative recovery of the patient is better.

As shown in FIG. 2, in the embodiment, the first connection portion is a first axial tooth portion 41; the second connection portion is a second axial tooth portion 51; the third connection portion is a third axial tooth portion 42; the fourth connection portion is a fourth axial tooth portion 52; the first axial tooth portion 41 is matched with the third axial tooth portion 42, so as to enable an angle between the prosthesis main body 10 and the connecting device to be adjustable; and the second axial tooth portion 51 is matched with the fourth axial tooth portion 52, so as to enable an angle between the acetabular cup 20 and the connecting device 30 to be adjustable. Specifically, when the doctor adjusts the position of the acetabular cup, the first axial tooth portion 41 and the third axial tooth portion 42 need to be buckled, i.e., the first axial tooth portion 41 is inserted into a groove of the third axial tooth portion 42. Likewise, the second axial tooth portion 51 and the fourth axial tooth portion 52 need to be buckled, i.e., the second axial tooth portion 51 is inserted into a groove of the fourth axial tooth portion 52. The above structure is simple and easy to assemble, so the operation time is shortened to a certain extent and the infection risk is reduced.

Of course, persons skilled in the art should understand the first connection portion, the second connection portion, the third connection portion and the fourth connection portion all may be not of an axial gear structure. An angle adjustment structure may be additionally increased between the first connection portion and the third connection portion, and it may be arranged on the first connection portion and/or the third connection portion. Likewise, another angle adjustment structure also may be additionally increased between the second connection portion and the fourth connection portion, and it may be arranged on the second connection portion and/or the fourth connection portion.

In the embodiment, the first axial tooth portion 41 and the third axial tooth portion 42 are connected together via a first fastener (not drawn in Fig.); and the second axial tooth portion 51 and the fourth axial tooth portion 52 are connected together via a second fastener (not drawn in Fig.). Preferably, the first fastener and the second fastener are screws. And the above structure is simple and easy to assemble.

In the embodiment, an inner wall of the acetabular cup 20 and a hemi-spherical polyethylene lining are spliced by means of bone cement. For ease of embedding the bone cement, as shown in FIG. 2, in the embodiment, an annular groove 21 is provided on the inner wall of the acetabular cup 20. And the above structure is simple and easy to implement.

As shown in FIG. 2, to better connect the acetabular cup 20 with the hemi-spherical polyethylene lining, in the embodiment, a plurality of through holes 22 are provided on a cup wall of the acetabular cup 20. With the above structure, the bone cement enters the through holes 22 to form an anchoring. And preferably, the number of the through holes 22 are 5-10.

As shown in FIG. 1 and FIG. 2, in the embodiment, the hipbone prosthesis further includes a plurality of screw-rod structures; each of the screw-rod structures include connecting seat 61, connecting seat 62 and a rod body 63; the connecting seat 61 is connected with a lumbar vertebral body; the connecting seat 62 is connected with the prosthesis main body 10; the rod body 63 is fixed on the connecting seat 61 and the connecting seat 62. By virtue of the above structure, the fixing between the prosthesis main body 10 and the lumbar vertebral body is reinforced, and the stability of the sacrum 1 is increased, thereby preventing a lumbar vertebra portion from going down.

Figure 3:
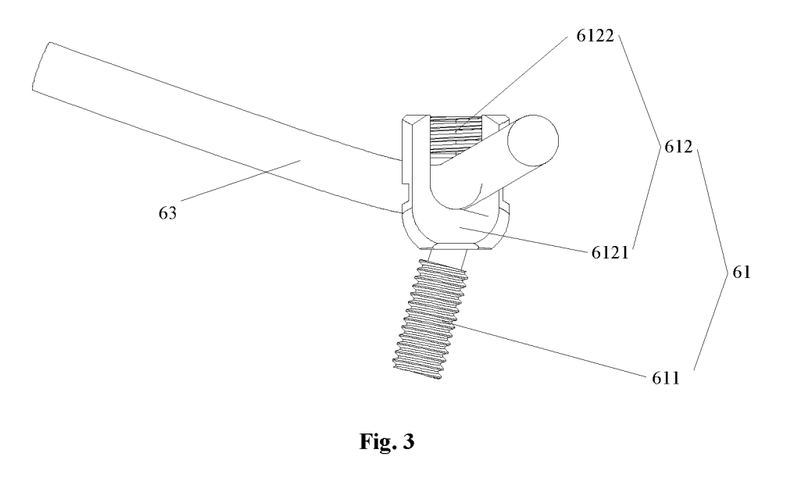
FIG. 3 shows a three-dimensional structure schematic diagram of a connecting seat of the hipbone prosthesis in FIG. 1.
Figure 4:
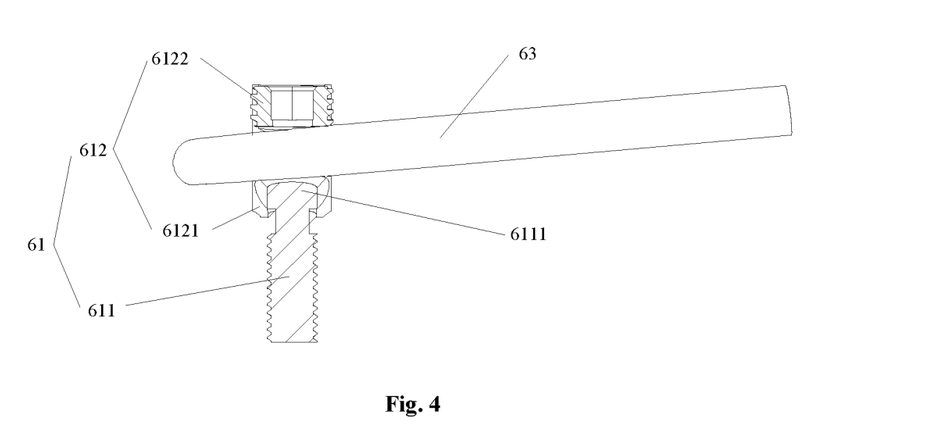
FIG. 4 shows a schematic diagram of a longitudinal section structure of the connecting seat in FIG. 3.

As shown in FIG. 3 and FIG. 4, in the embodiment, the connecting seat 61 includes: a connecting screw 611, one end of the connecting screw 611 being connected with the lumbar vertebral body, and the other end of the connecting screw 611 being provided with a spherical screw head 6111; and a rod body fixing portion 612, configured to fix the rod body 63, one end of the rod body fixing portion 612 being provided with a spherical hole matched with the spherical screw head 6111 so that the rod body fixing portion 612 is rotatably arranged on the connecting screw 611. With the above structure, the rod body fixing portion 612 is rotatably arranged on the connecting screw 611, so the doctor may adjust a position of the rod body 63 according to an actual demand, and thus, an installation position is more accurate and an installation process is simpler.

Figure 5:
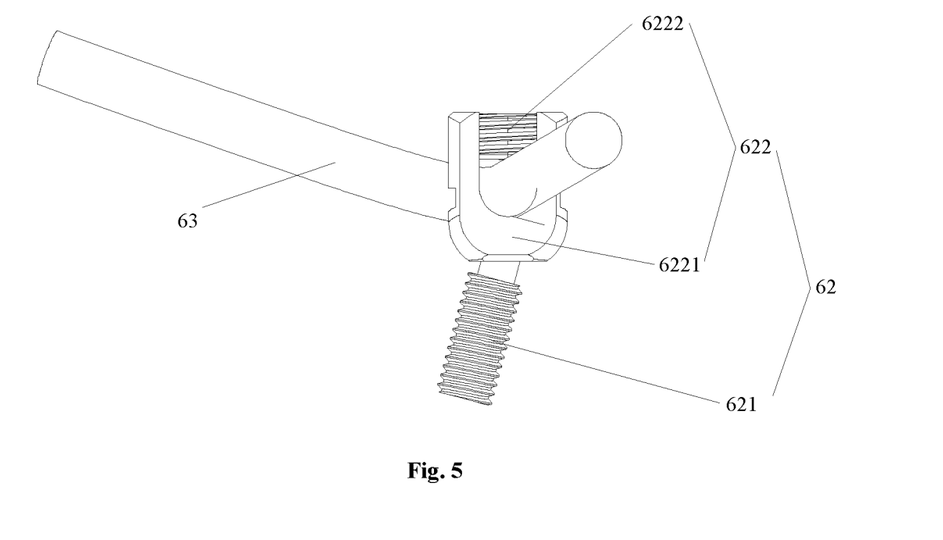
FIG. 5 shows a three-dimensional structure schematic diagram of another connecting seat of the hipbone prosthesis in FIG. 1.
Figure 6:
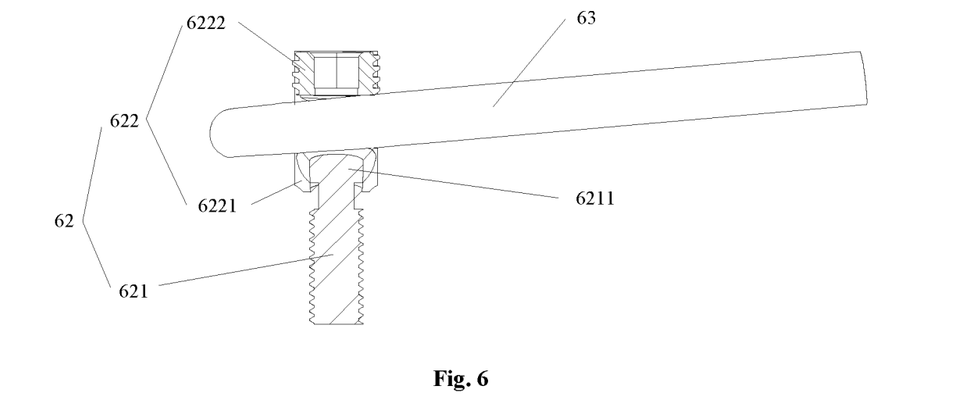
FIG. 6 shows a schematic diagram of a longitudinal section structure of the connecting seat in FIG. 5.

As shown in FIG. 5 and FIG. 6, in the embodiment, the connecting seat 62 includes: a connecting screw 621, one end of the connecting screw 621 being connected with the prosthesis main body 10, and the other end of the connecting screw 621 being provided with a spherical screw head 6211; and a rod body fixing portion 622, configured to fix the rod body 63, one end of the rod body fixing portion 622 being provided with a spherical inner wall matched with the spherical screw head 6211 so that the rod body fixing portion 622 is rotatably arranged on the connecting screw 621. With the above structure, the rod body fixing portion 622 is rotatably arranged on the connecting screw 621, so the doctor may adjust a position of the rod body 63 according to an actual demand, and thus, an installation position is more accurate and an installation process is simpler.

As shown in FIG. 3 and FIG. 4, in the embodiment, the rod body fixing portion 612 includes a U-shaped support 6121 and a fixing cap 6122; and the rod body 63 is arranged between the U-shaped support 6121 and the fixing cap 6122 in a clamping manner. Specifically, an installation space is formed in an U-shaped inner wall of the U-shaped support 6121, and the rod body 63 is inserted into the installation space. An upper part of the U-shaped inner wall of the U-shaped support 6121 is provided with an inner screw thread, and the fixing cap 6122 is provided with an outer screw thread matched with the inner screw thread of the U-shaped support 6121. When the rod body 63 is installed, it is necessary to first enable the rod body 63 to go through the installation space and then screw the fixing cap 6122 to the U-shaped support 6121. Therefore, the above structure is simple, and convenient to install.

As shown in FIG. 5 and FIG. 6, in the embodiment, the rod body fixing portion 622 includes a U-shaped support 6221 and a fixing cap 6222; and the rod body 63 is arranged between the U-shaped support 6221 and the fixing cap 6222 in a clamping manner. Specifically, an installation space is formed in an U-shaped inner wall of the U-shaped support 6221, and the rod body 63 is inserted into the installation space. An upper part of the U-shaped inner wall of the U-shaped support 6221 is provided with an inner screw thread, and each of the fixing cap 6222 are provided with an outer screw thread matched with the inner screw threads of the U-shaped support 6221. When the rod body 63 is installed, it is necessary to first enable the rod body 63 to go through the installation space and then screw the fixing cap 6222 to the U-shaped support 6221. Therefore, the above structure is simple, and convenient to install.

As shown in FIG. 1 and FIG. 2, in the embodiment, a plurality of screw holes 111 are formed in the first end portion 11; a plurality of screw seats are respectively arranged in the screw holes 111; and each of the screw seats is provided with a spherical inner surface. When the doctor needs to fix the prosthesis main body 10 onto the sacrum 1 via a plurality of screws, each of the screws is respectively penetrated into the screw holes 111 first. As each of the screw holes 111 is conical hole, head portion of each of the screws is spherical head and each of the screw seats is provided with the spherical inner surface matched with the spherical head, the screws can be rotated in a specifically range, and the doctor may choose nailing directions of the screws in terms of a practical condition. With the above structure, the doctor can choose screw fixing positions according to the practical condition, so that the fixing effect between the prosthesis main body 10 and the sacrum 1 is better.

Preferably, in the embodiment, the prosthesis main body 10 is of a hollow truss structure. On one hand, the truss structure can greatly reduce the weight of the prosthesis main body 10 and improves the material utilization rate, and simultaneously further can guarantee the strength and the rigidity of the prosthesis main body 10. On the other hand, with the adoption of the above structure, the prosthesis main body 10 is closer to an adjacent skeleton, so that the bony fusion effect is better. Because anatomic reconstruction after the pelvic tumor excision needs to satisfy the accurate and complex requirements, and even further needs to satisfy the disposable and tailor-made requirements, the prosthesis main body 10 is prototyped by means of 3D printing in the embodiment. And the above process intrinsically has the characteristics of being accurate, being capable of manufacturing a complex part and being capable of personally customized.

It is to be noted that a Three-Dimensional (3D) printing rapid prototyping technology is a brand-new manufacturing technology based on a material stacking method, is different from the traditional removed material processing technology, and is also referred to as additive manufacturing (AKYCM, AKYCdditive MAKYCnufAKYCcturing). The 3D printing technology is to stack layers of a material into an entity via a rapid prototyping machine by employing 3D CAKYCD data. It is named because though different types of rapid prototyping systems have different prototyping principles and system characteristics depending on different prototyping materials used, their basic principles are the same and are to "manufacture in layers and overlap one by one", just like a "3D printer". With the rapid development of cutting-edge technologies such as manufacturing technology, digital modeling technology, numerical control technology, information technology, material science technology, chemical and biological technologies as well as the multidisciplinary close cooperation, the development of the 3D printing technology has become one of the most popular new technologies at present. The 3D printing will have a broad application prospect in the orthopedics field in future because its characteristics meet special requirements of the orthopedics. On one hand, bone tissues are a typical example of a complex structure, and it is very hard for the existing bionic technology to copy their special 3D forms and physiological functions. However, the 3D printing is just suitable for the rapid manufacturing of the complex structure and can obtain an approximately ideal bone repair material. And on the other hand, human bodies have a highly individual specificity, the traditional medical products produced in large scale and in batches cannot meet the personalized requirement and the former personalized and customized products produced by means of a manufacturing process such as mould have a high cost and a long period. Following the widespread application of a digital imaging technology in the medical field, the skeleton is an organ easiest to obtain an accurate digital image; and by combining with the skeleton and the 3D printing, the personalized medical products may be produced accurately and rapidly at a low cost. Therefore, by virtue of the 3D printing technology, an implant product with any form and an ideal biomechanical strength can be casted in a short time, making the development of personalized and customized bone implant products become true.

In the embodiment, the first end portion 11 is provided with a bio-coating (not shown in Fig.). The above structure can rapidly promote the generation of bone cells and is easily integrated with the bone (sacrum), thereby achieving the medium-long term fixing effect. Compared with the traditional operation mode, it has the characteristics of high strength, high stability and strong bone integration capability.

In the embodiment, the first end portion 11 is provided with a first needle-like bump (not shown in Fig.). The needle-like bump has the effects of cutting and anchoring, so that the sacrum 1 is fixed with the first end portion 11 of the prosthesis main body 10 together.

Figure 7:
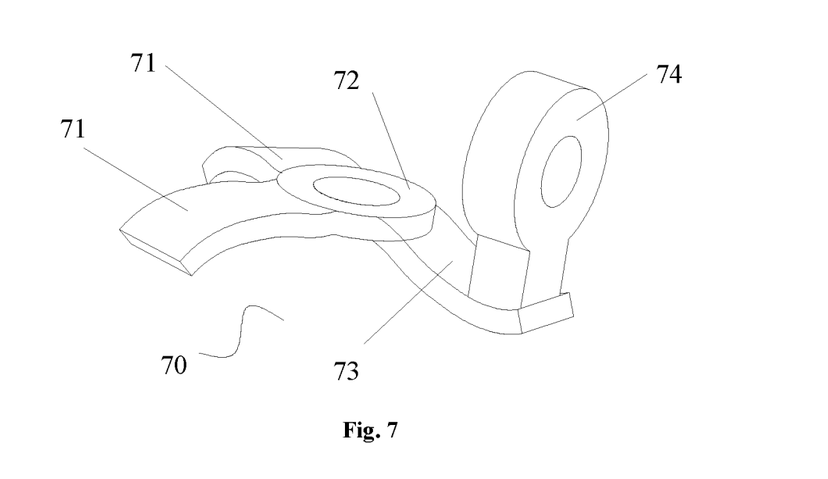
FIG. 7 shows a three-dimensional structure schematic diagram of an anti-dropping mechanism of the hipbone prosthesis in FIG. 1.

As shown in FIG. 7, in the embodiment, a plurality of anti-dropping mechanisms 70 are arranged on the prosthesis main body; each of the anti-dropping mechanisms 70 is respectively arranged between the prosthesis main body and the connecting seat 62 in a clamping manner; and each of the anti-dropping mechanisms 70 includes a plurality of first anti-dropping tentacles 71 matched with the screws accommodated in the screw holes 111. When the connecting seat 62 is screwed tightly in use, the first anti-dropping tentacles 71 are propped against the screws accommodated in the screw holes 111. The tighter the connecting screw 621 of the connecting seat 62 is, the greater a force that the first anti-dropping tentacles 71 are propped against the screws is. Therefore, the above structure can prevent the screws from dropping out from the screw holes 111. In addition, it is common that the connecting screw 621 screwed to the bone is loosen in the related technology, so the anti-dropping mechanisms 70 further can provide a pretightening force for the connecting seat 62 so as to prevent the looseness of the connecting seat 62.

As shown in FIG. 7, in the embodiment, each of the anti-dropping mechanisms 70 further includes an anti-dropping main body 72; the anti-dropping main body 72 is arranged between the prosthesis main body and the connecting seat 62 in a clamping manner; each of the anti-dropping mechanisms 70 further includes a second anti-dropping tentacle 73; the first anti-dropping tentacles 71 and the second anti-dropping tentacle 73 are connected with the anti-dropping main body 72 and are extended outward; and a limiting sleeve 74 matched with the rod body 63 is arranged on the second anti-dropping tentacle 73. Preferably, multiple first anti-dropping tentacles 71 matched with the screw holes 111 are provided. Because the multiple first anti-dropping tentacles 71 are extended outward to the screw holes 111, and the anti-dropping main body 72 is arranged between the prosthesis main body and the connecting seat 62 in a clamping manner, the anti-dropping mechanisms 70 are limited and cannot be rotated. And the limiting sleeve 74 is arranged on the second anti-dropping tentacle 73 and the limiting sleeve 74 is matched with the rod body 63, so the rod body 63 is also limited and cannot be rotated. Therefore, the above structure prevents the rotation of the rod body 63, thereby increasing the stability of the system.

Preferably, each of the anti-dropping mechanisms 70 is leaf springs; tail end of the second anti-dropping tentacle 73 of each of the leaf springs is tilted upward; and the limiting sleeve 74 is arranged at the tail end of the second anti-dropping tentacle 73.

The above description is only preferred embodiments of the present disclosure and is not intended to limit the present disclosure. Persons in the art can make various modifications and changes of the present disclosure. Any modification, equivalent replacement, or improvement made within the spirit and principle of the present disclosure shall all fall within the protection scope of the present disclosure.

What is claimed is:

1. A hipbone prosthesis, comprising:
a prosthesis main body, the prosthesis main body being of an arched structure, the prosthesis main body comprising a first end portion and a second end portion, and the first end portion is configured to contact and match with a sacrum (1); and
an acetabular cup (20) and a connecting device (30), the acetabular cup (20) being connected with the second end portion in a position adjustable manner via the connecting device (30), the hipbone prosthesis further comprises a screw-rod structure; the screw-rod structure comprises a connecting seat (62) and a rod body (63); the connecting seat (62) is connected with the prosthesis main body (10); the rod body (63) is fixed on the connecting seat (62); a screw hole (111) is formed in the first end portion (11); a screw seat is arranged in the screw hole (111); anti-dropping mechanism (70) is arranged on the prosthesis main body (10); the anti-dropping mechanism (70) is arranged between the prosthesis main body (10) and the connecting seat (62) in a clamping manner; and the anti-dropping mechanism (70) comprises a first anti-dropping tentacle (71) matched with a screw accommodated in the screw hole (111); the anti-dropping mechanism (70) further comprises an anti-dropping main body (72); the anti-dropping main body (72) is arranged between the prosthesis main body (10) and the connecting seat (62) in a clamping manner; the anti-dropping mechanism (70) further comprises a second anti-dropping tentacle (73); the first anti-dropping tentacle (71) and the second anti-dropping tentacle (73) are connected with the anti-dropping main body (72) and are extended outward; and a limiting sleeve (74) matched with the rod body (63) is arranged on the second anti-dropping tentacle (73).

2. The hipbone prosthesis as claimed in claim 1, wherein the connecting device (30) comprises a first connection portion and a second connection portion; a central line of the first connection portion and a central line of the second connection portion form an angle; the second end portion is provided with a third connection portion connected with the first connection portion; and the acetabular cup (20) is provided with a fourth connection portion connected with the second connection portion.

3. The hipbone prosthesis as claimed in claim 2, wherein the first connection portion is a first axial tooth portion (41); the second connection portion is a second axial tooth portion (51); the third connection portion is a third axial tooth portion (42); the fourth connection portion is a fourth axial tooth portion (52); the first axial tooth portion (41) is matched with the third axial tooth portion (42), so as to enable an angle between the prosthesis main body (10) and the connecting device (30) to be adjustable; and the second axial tooth portion (51) is matched with the fourth axial tooth portion (52), so as to enable an angle between the acetabular cup (20) and the connecting device (30) to be adjustable.

4. The hipbone prosthesis as claimed in claim 3, wherein the first axial tooth portion (41) and the third axial tooth portion (42) are connected together via a first fastener; and the second axial tooth portion (51) and the fourth axial tooth portion (52) are connected together via a second fastener.

5. The hipbone prosthesis as claimed in claim 1, wherein an annular groove (21) is provided on an inner wall of the acetabular cup (20).

6. The hipbone prosthesis as claimed in claim 1, wherein a plurality of through holes (22) are provided on a cup wall of the acetabular cup (20).

7. The hipbone prosthesis as claimed in claim 1, wherein the screw seat is provided with a spherical inner surface.

8. The hipbone prosthesis as claimed in claim 1, wherein the connecting seat (62) comprises:
a connecting screw (621), one end of the connecting screw (621) being connected with the prosthesis main body (10), and the other end of the connecting screw (621) being provided with a spherical screw head; and
a rod body fixing portion (622) configured to fix the rod body (63), one end of the rod body fixing portion (622) being provided with a spherical inner wall matched with the spherical screw head so that the rod body fixing portion (622) is rotatably arranged on the connecting screw (621).

9. The hipbone prosthesis as claimed in claim 8, wherein the rod body fixing portion (622) comprises a U-shaped support (6221) and a fixing cap (6222); and the rod body (63) is arranged between the U-shaped support (6221) and the fixing cap (6222) in a clamping manner.

* * * * *